United States Patent
Zhi et al.

(10) Patent No.: US 6,358,947 B1
(45) Date of Patent: Mar. 19, 2002

(54) TETRACYCLIC PROGESTERONE RECEPTOR MODULATOR COMPOUNDS AND METHODS

(75) Inventors: Lin Zhi, San Diego; Todd K. Jones, Solana Beach, both of CA (US); Jay E. Wrobel, Lawrenceville, NJ (US); Christopher M. Tegley, Thousand Oaks, CA (US); Andrew Fensome, Wayne; Puwen Zhang, Audubon, both of PA (US); James P. Edwards, San Diego, CA (US)

(73) Assignees: American Home Products Corporation, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/552,353

(22) Filed: Apr. 19, 2000

Related U.S. Application Data

(60) Provisional application No. 60/183,044, filed on May 4, 1999.

(51) Int. Cl.$^7$ .................. C07D 498/02; C07D 471/02; A61K 31/542; A61K 31/5365; A61P 5/24
(52) U.S. Cl. .................. 514/229.5; 544/99; 544/95
(58) Field of Search .................. 514/229.5; 544/95, 544/99

(56) References Cited

U.S. PATENT DOCUMENTS

| | | | |
|---|---|---|---|
| 3,635,964 A | 1/1972 | Skorcz et al. ............. | 260/247.1 |
| 3,917,592 A | 11/1975 | Kobzina ............. | 260/244 |
| 4,093,730 A | 6/1978 | Butti ............. | 424/270 |
| 4,440,785 A | 4/1984 | Walsh ............. | 424/317 |
| 4,666,913 A | 5/1987 | Kubla et al. ............. | 514/259 |
| 4,670,566 A | 6/1987 | Walsh ............. | 548/485 |
| 4,721,721 A | 1/1988 | Kuhla ............. | 514/312 |
| 4,822,794 A | 4/1989 | Spada ............. | 514/230 |
| 4,831,027 A | 5/1989 | Narr et al. ............. | 514/212 |
| 4,853,473 A | 8/1989 | Fischer et al. ............. | 549/326 |
| 5,007,952 A | 4/1991 | Kume et al. ............. | 71/73 |
| 5,171,851 A | 12/1992 | Kim et al. ............. | 544/50 |
| 5,414,088 A | 5/1995 | Von Der Saal et al. ..... | 546/158 |
| 5,453,516 A | 9/1995 | Fischer et al. ............. | 548/543 |
| 5,475,020 A | 12/1995 | Johnson et al. ............. | 548/466 |
| 5,521,166 A | 5/1996 | Grubb ............. | 514/170 |
| 5,681,817 A | 10/1997 | Hodgen et al. ............. | 514/12 |
| 5,688,808 A | 11/1997 | Jones et al. ............. | 514/285 |
| 5,688,810 A | 11/1997 | Jones et al. ............. | 514/311 |
| 5,693,646 A | 12/1997 | Jones et al. ............. | 514/285 |
| 5,693,647 A | 12/1997 | Jones et al. ............. | 514/285 |
| 5,696,127 A | 12/1997 | Jones et al. ............. | 514/285 |
| 5,696,130 A | 12/1997 | Jones et al. ............. | 514/291 |
| 5,696,133 A | 12/1997 | Pooley et al. ............. | 514/314 |
| 5,719,136 A | 2/1998 | Chwalisz et al. ............. | 514/170 |
| 5,733,902 A | 3/1998 | Schneider ............. | 514/177 |
| 5,808,139 A | 9/1998 | Pathirana ............. | 560/138 |
| 5,874,430 A | 2/1999 | Christ ............. | 514/229.8 |
| 6,077,840 A | 6/2000 | Kurihara ............. | 514/232.8 |

FOREIGN PATENT DOCUMENTS

| | | |
|---|---|---|
| DE | 3633861 | 4/1988 |
| DE | 43 30 234 | 3/1995 |
| DE | 43 44 463 | 6/1995 |
| EP | 022317 | 1/1981 |
| EP | 0 208 510 | 1/1987 |
| EP | 311135 | 4/1989 |
| EP | 385850 | 9/1990 |
| EP | 483077 | 9/1991 |
| EP | 454330 | 10/1991 |
| EP | 0 535 529 | 9/1992 |
| EP | 510235 | 10/1992 |
| EP | 947 507 | 10/1999 |
| EP | 978 279 | 2/2000 |
| JP | 63112584 | 5/1988 |
| WO | WO 86/03749 | 7/1986 |
| WO | WO 91/04974 | 4/1991 |
| WO | WO 91/06545 | 5/1991 |
| WO | WO 93/12085 | 6/1993 |
| WO | WO 94/14434 | 7/1994 |
| WO | WO 94/29272 | 12/1994 |
| WO | WO 95/11013 | 4/1995 |
| WO | WO 95/20389 | 8/1995 |
| WO | WO 95/20972 | 8/1995 |
| WO | WO 95/33746 | 12/1995 |
| WO | WO 96/15794 | 5/1996 |
| WO | WO 96/19458 | 6/1996 |
| WO | WO 96/19997 | 7/1996 |
| WO | WO 97/13767 | 4/1997 |
| WO | WO 97/49407 | 12/1997 |
| WO | WO 98/14436 | 4/1998 |
| WO | WO 98/27059 | 6/1998 |
| WO | WO 98/55116 | 12/1998 |
| WO | WO 99/10325 | 3/1999 |
| WO | WO 99/11264 | 3/1999 |
| WO | WO 99/15500 | 4/1999 |
| WO | WO 99/44608 | 9/1999 |

OTHER PUBLICATIONS

R. M. Evans, "The Steroid and Thyroid Hormone Receptor Superfamily", *Science*, 240:889 (May 13, 1988).

A. Ulmann et al., "Clinical Uses of Mifepristone (MFP)", *Ann. N.Y. Acad. Sci.*, 261:248 (Jun. 12, 1995).

R. Kekkonen et al., "Sequential Regiment of the Antiprogesterone RU486 and Synthetic Progestin for Contraception", *Fertility and Sterility*, 60(4):610 (Oct.1993).

(List continued on next page.)

*Primary Examiner*—Mark L. Berch
*Assistant Examiner*—Kahsay Habte
(74) *Attorney, Agent, or Firm*—Howson and Howson

(57) ABSTRACT

Nonsteroidal compounds that are high affinity, high selectivity modulators for progesterone receptors are disclosed. Also disclosed are pharmaceutical compositions incorporating such compounds, methods for employing the disclosed compounds and compositions for treating patients requiring progesterone receptor agonist, partial agonist or antagonist therapy, intermediates useful in the preparation of the compounds and processes for the preparation of the progesterone receptor modulator compounds.

10 Claims, No Drawings

OTHER PUBLICATIONS

K. Horwitz et al., "Progestin, Progesterone Receptors, and Breast Cancer", "Horm. Cancer", publisher: Birkhaeuser, Boston, Mass., ed. Vedeckis, p. 283–306 (1996) abstract only.

A. A. Murphy et al., "Regression of Uterine Leiomyomata in Response to the Antiprogesterone RU 486", *J. Clin. Endo. Metab.*, 76(2):513 (Feb. 1993).

L. M. Kettel et al., "Endocrine Responses to Long–Term Administration of the Antiprogesterone RU486 in Patients with Pelvic Endometriosis", *Fertility and Sterility*, 56(3):402 (Sep. 1991).

H. Michna et al., "Differentiation Therapy with Progesterone Antagonists", *Ann. N.Y. Acad. Sci.*, 761:224 (Jun. 1995).

L. Zhi et al., "5–Aryl–1,2–Dihydrochromeno[3,4–f]quinolines: A Novel Class of Nonsteroidal Human Progesterone Receptor Agonists", *J. Med. Chem.*, 41(3):291 (Oct. 22, 1998).

D. W. Combs et al., "Nonsteroidal Progesterone Receptor Ligands. 2. High–Affinity Ligands with Selectivity for Bone Cell Progesterone Receptors", *J. Med. Chem.*, 38:4880 (Dec. 8, 1995).

K. L. Perlman et al., "20–Oxopregnacalciferols: Vitamin D Compounds that Bind the Progesterone Receptor", *Tet. Letters*, 35(15):2295 (1994).

L. G. Hamann et al., "Synthesis and Biological Activity of Novel Nonsteroidal Progesterone Receptor Antagonists", *Ann. N.Y. Acad. Sci.*, 761:383 (Jun. 12, 1995).

R. H. K. Chen et al., "Synthesis and SAR of a Novel Series of Spirobenzothlzaepine Derivatives with Antiprogestin Activity", POI–37, 16$^{th}$ Int. Cong. Het. Chem., Montana (1997).

B. Narr et al., "Preparation, Testing and Formulation of Imidazobenzoxazinones as Cardiotonics", *Chemical Abstracts*, 109:22973 (1988).

R. J. Hartmann et al., "Effects of Brofoxine, A New Anxiolytic on Experimentally Induced Conflict in Rats", *Proc West. Pharmacol. Soc.*, 21:51–55 (1978).

B. Singh et al., "Novel cAMP PDE III Inhibitor: Imidazo[4,5–b]pyridin–2(3H)–ones and Thiazolo[4,5–b]pyridin–2(3H)–ones and Their Analogs", *J. Med. Chem.*, 37:248 (Jan. 21, 1994).

A. Andreani et al., "Potential Antitumor Agents XVII (1). Cytotoxic Agents from Indole Derivatives and Their Intermediates", *Acta. Pharm. Nord.*, 2(6):407 (1990).

Sakata et al., "Silver Halide Photographic Materials Useful for Platemaking", *Chemical Abstracts*, 123:301431 (1993).

P. Pflegel et al., "Polarografie con 7–Chlor–5 phenyl–2–thioxo–1H–2,3–dihydro–1,3,4–benzotriazepinen", *Pharmazie*, 37(10): 714–717 (1982).

E. I. Barengolts et al., "Progesterone Antagonist RU 486 Has Bone–Sparing Effects in Ovariectomized Rats", *Bone*, 17(1):21 (Jul. 1995).

E. V. Gromachevskaya et al., "Studies of 4H–3, 1–Benzoxazines", *Chem. Heterocycl. Cmpds.* 33(10):1209–1214 (1997).

D. Chiarino et al., "2, 1–Benzisothiazoline 2, 2–Dioxide and Derivatives", *J. Heterocycl. Chem.*, 23(6):1645–1649 (Nov.–Dec. 1986).

A. Turck et al., "On the Metabolism of 3–Substituted and 3,6–Disubstituted Pyridazines", *Tetrahedron*, 49(3):599–606 (1993).

V. Kumar et al., "Synthesis of 7–Azaindole and 7–Azaoxindole Derivatives through a Palladium–Catalyzed Cross–Coupling Reaction", *J. Org. Chem.*, 57(25):6995–6998 (1992).

P. Canonne et al., "Spirocyclization of 1–(o–Aminophenyl)cycloalkanols and 1–(2'–Amino–3'–pyridinyl)cycloalkanols", *J. Heterocyclic Chem.*, 26:113 (Jan.–Feb. 1989).

M–C. Forest et al., "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", *J. Med. Chem.*, 35:163–172 (Jan. 1992).

D. W. Combs et al., "Heteroatom Analogues of Bemoradan: Chemistry and Cardiotonic Activity of 1, 4–Benzothiazinylpyridazinones", *J. Med. Chem.*, 35:172–176 (Jan. 1992).

Kurihari et al., "Synthesis of (±)–PF1092A, B, and C; New Nonsteroidal Progesterone Receptor Ligands", *J. Antibiotics*, 50(4):360 (Apr. 1997).

A. Kende et al., "Regioselective C–3 Alkylation of Oxindole Dianion", *Synth. Commun.* 12(1):1 (1982).

T. Tucker et al., "Synthesis of a Series of 4–(Arylethylnyl)–6–Chloro–4–Cyclopropyl–3, 4–dihydroquinazolin–2(1H)–ones as Novel Non–Nucleoside HIV–1 Reverse Transcriptase Inhibitors", *J. Med. Chem.*, 37:2347–2444 Jul. 22, 1994.

J. P. Edwards et al., "5–Aryl–1,2–Dihydro–5H–Chromeno [3,4–f]Quinolines as Potent, Orally Active, Nonsteroidal Progesterone Receptor Agonists: The Effect of D–Ring Substituents", *J. Med. Chem.*, 41:303–310 (Jan. 29, 1998).

Derwent WPI abstract, "New Imidazo–Pyridine Derivatives—Useful as Platelet Agglutination Inhibitor, Antiallergic, Antiinflammatory Sedative, Cardiac, and Cardiovascular Vasodilators", JP 63112584.

Derwent WPI abstract, N. Brumagniez et al., "Benzimidazole and Azabenzimidazole(s)—Having Cardiotonic, Vasodilating, Anti–Hypertensive, Anti–Aggregation, and Anti–Ulcer Activity", EP 385850.

Derwent WPI abstract, F. Arndt et al., "New Heterocycle substituted Benzo–Fused Azine and Azole Derivatives—Useful as Selective Herbicides for Pre or Post–Emergence Application", EP 311135.

K. Horwitz et al., "Progestin, Progesterone Receptors, and Breast Cancer", "Hormones and Cancer", publisher: Birkhaeuser, Boston, Mass., ed. Vedeckis, p. 283–306 (1996).

Mamaev, V. P., et al., "Synthesis of 4H–Thieno [3, 2–B] Pyrrol–5(6H)–One" Bulletin of the Academy of Sciences on the USSR. Division of Chemical Science, US, Consultants Bureau, New York, vol. 9, p. 1549–1553, 1996.

Derwent WPI Abstract, Chwalisz, K., et al. "Female Contraceptive Method Comprises Gestation Treatment with Intermittent Progesterone Antagonist Administration. ", DE 4,330,234.

Derwent WPI Abstract, Chwalisz, K., et al. "Contraceptive Pack for Implantation Inhibition –Contains Competitive Progesterone Antagonist and Gestagen for Sequential Oral Administration.", DE 4,44,463.

Kolasa, K., et al., "Preliminary Pharmacological Studies of the Central Action of Phenyl and Piperidinomethyl Derivatives of 2–Benzoxazolone." *Chemical Abstracts*, vol. 99, No. 1, Abst. No. 157a, Jul. 4, 1983.

Meanwell N. A., et al., "Regiospecific Functionalization of 1, 3–dihydro–2H–Benzimidazol–2–One and Structurally Related Cyclic Urea Derivatives" *J. Organic Chem.*, 60(6): 1565–82 (Mar. 24, 1995).

Singh, B., et al., "An Efficient and Novel Synthesis of Fused Thiazol–2(3H)–ones" *Heterocycles*, 36(1): 133–134, p. 136, compounds 16a, 18a, Jan. 1993.

Vernin, G., et al., "Etude Dans la Serie des Radicaux Heterocycliques. Partie XV. Decomposition aprotique de l' amino–6–ethyl–2–benzothiazole dans des substrats aromatiques et heteroaromatiques: preparation des mesityl–6–et furyl–6–ethyl–2–benzothiazoles, des sels quaternaires et des spiropyrannes correspondants" *Helvetica Chimica Acta*, 62(1/3):21–30 Jan. 24, 1979.-

TETRACYCLIC PROGESTERONE RECEPTOR MODULATOR COMPOUNDS AND METHODS

CROSS REFERENCE TO RELATED APPLICATION

This application claims the benefit of the priority U.S. Provisional Patent Application No. 60/183,044, filed May 4, 1999.

FIELD OF THE INVENTION

This invention relates to nonsteroidal tetracyclic compounds that are modulators (i.e. agonists and antagonists) of progesterone receptors, and to methods for the making and use of such compounds.

BACKGROUND OF THE INVENTION

Progesterone receptor (PR) modulators have been widely used in regulation of female reproduction systems and in treatment of female hormone dependent diseases. The effectiveness of known steroidal PR modulators is often tempered by their undesired side-effect profile, particularly during long-term administration. For example, the effectiveness of synthetic progestins, such as norgestrel, as female birth control agents must be weighed against the increased risk of breast cancer and heart disease to women taking such agents. Similarly, the progesterone antagonist, mifepristone (RU486), if administered for chronic indications, such as uterine fibroids, endometriosis and certain hormone-dependent cancers, could cause homeostatic imbalances in a patient due to its inherent cross-reactivity as a glucocorticoid receptor (GR) antagonist. Accordingly, identification of compounds that have good specificity for PR, but have reduced or no cross-reactivity for other steroid receptors, would be of significant value in the improvement of women's health.

Nonsteroidal molecules that contain a di- or tetrahydroquinoline ring as the core pharmacophore have been described as steroid receptor modulator compounds. {See for example: "Preparation of Quinolines and Fused Quinolines as Steroid Receptor Modulators", T. K. Jones, M. E. Goldman, C. L. F. Pooley, D. T. Winn, J. P. Edwards, S. J. West, C. M. Tegley, L. Zhi, L. G. Hamann, R. L. Davis, L. J. Farmer, PCT Int. Appl. Pub. No. WO 96/19458; "Steroid Receptor Modulator Compounds and Methods", T. K Jones, D. T. Winr, L. Zhi, L. G. Hamann, C. M. Tegley, C. L. F. Pooley, U.S. Pat. No. 5,688,808; "Steroid Receptor Modulator Compounds and Methods", T. K Jones, M. E. Goldman, C. L. F. Pooley, D. T. Winn, J. P. Edwards, S. J. West, C. M. Tegley, L. Zhi, U.S. Pat. No. 5,688,810; "Steroid Receptor Modulator Compounds and Methods", T. K Jones, C. M. Tegley, L. Zhi, J. P. Edwards, S. J. West, U.S. Pat. No. 5,693,646; "Steroid Receptor Modulator Compounds and Methods", T. K Jones, L. Zhi, C. M. Tegley, D. T. Winn, L. G. Hamann, J. P. Edwards, S. J. West, U.S. Pat. No. 5,693,647; "Steroid Receptor Modulator Compounds and Methods", T. K Jones, L. Zhi, J. P. Edwards, C. M. Tegley, S. J. West, U.S. Pat. No. 5,696,127; "Steroid Receptor Modulator Comnpounds and Methods", T. K Jones, D. T. Winn, M. E. Goldman, L. G. Hamann, L. Zhi, L. J. Farmer, R. L. Davis, U.S. Pat. No. 5,696,130; "Steroid Receptor Modulator Compounds and Methods", T. K Jones, M. E. Goldman, C. L. F. Pooley, D. T. Winn, J. P. Edwards, S. J. West, C. M. Tegley, L. Zhi, L. G. Hamann, L. J. Farmer, R. L. Davis, U.S. Pat. No. 5,696,133.} Molecules containing a bicyclic heterocycle have been reported as cardiotonic agents. {See: "A Novel Class of Cardiotonic Agents: Synthesis and Biological Evaluation of 5-Substituted 3,6-Dihydrothiadiazin-2-ones with Cyclic AMP Phosphoidesterase Inhibiting and Myofibrillar Calcium Sensitizing Properties", M.-C. Forest, P. Lahouratate, M. Martin, G. Nadler, M. J. Quiniou, R G. Zimmermann, J. Med. Chem. 35 (1992) 163–172; "Heteroatom Analogues of Bemoradan: Chemistry and Cardiotonic Activity of 1,4-Benzothiazinylpyridazinones", D. W. Combs, M. S. Rampulla, J. P. Demers, R. Falotico, J. B. Moore, J. Med. Chem., 35 (1992) 172–176.}

SUMMARY OF THE INVENTION

The present invention is directed to compounds, pharmaceutical compositions, and methods for modulating processes mediated by PR. More particularly, the invention relates to nonsteroidal compounds and compositions that are high affinity, high specificity agonists, partial agonists (i.e., partial activators and/or tissue-specific activators) and antagonists for progesterone receptors. Also provided are methods of making such compounds and pharmaceutical compositions, as well as critical intermediates used in their synthesis.

These and various other advantages and features of novelty that characterize the invention are pointed out with particularity in the claims annexed hereto and forming a part hereof However, for a better understanding of the invention, its advantages, and objects obtained by its use, reference should be had to the accompanying descriptive matter, in which preferred embodiments of the invention are described.

DETAILED DESCRIPTION OF THE INVENTION

As used herein, the following terms are defined with the following meanings, unless explicitly stated otherwise.

The terms alkyl, alkenyl, alkynyl and allyl include optionally substituted straight-chain, branched-chain, cyclic, saturated and/or unsaturated structures, and combinations thereof.

The term haloalkyl refers to alkyl structures, including straight-chain, branched-chain, or cyclic structures, or combinations thereof, that are substituted with one or more fluorines, chlorines, bromines or iodines, or combinations thereof.

The term heteroalkyl includes straight-chain, branched-chain, cyclic, saturated and/or unsaturated structures, or combinations thereof, in which one or more skeletal atoms is oxygen, nitrogen, sulfur, or combinations thereof.

The term aryl refers to an optionally substituted six-membered aromatic ring.

The term heteroaryl refers to an optionally substituted, aromatic five-membered heterocyclic ring containing one or more heteroatoms selected from the group consisting of oxygen, nitrogen and sulfur, or to an optionally substituted, aromatic six-membered heterocyclic ring containing one or more nitrogens.

The substituents of an "optionally substituted" structure include, but are not limited to, one or mnore of the following preferred substitutents: F, Cl, Br, I, CN, $NO_2$, $NH_2$, $NCH_3$, OH, $OCH_3$, $OCF_3$, $CH_3$, $CF_3$.

Compounds of the present invention are defined as those having the formula:

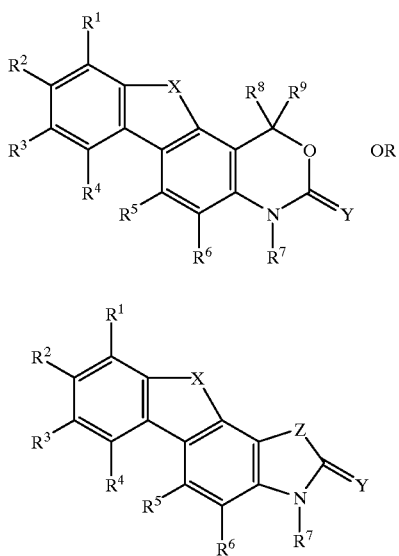

wherein:
R¹ through R⁶ are independently hydrogen, F, Cl, Br, I, NO₂, CN, OR¹⁰, NR¹⁰R¹¹, SR¹⁰, COR¹², CO₂R¹², CONR¹⁰OR¹¹, optionally substituted $C_1$ to $C_6$ alkyl or heteroalkyl, $C_1$ to $C_6$ haloalkyl, optionally substituted $C_3$ to $C_8$ cycloalyl, optionally substituted $C_2$ to $C_6$ alkenyl or allynyl, optionally substituted allyl, optionally substituted aryl or heteroaryl, or optionally substituted arylmethyl, where $R^{10}$ and $R^{11}$ are independently hydrogen, $C_1$ to $C_6$ alkyl or heteroalkyl or haloalkyl, aryl, heteroaryl, optionally substituted allyl, optionally substituted arylmethyl, COR¹³, SO₂R¹³ or S(O)R¹³, where $R^{12}$ is hydrogen, $C_1$ to $C_6$ aLkyl or heteroalkyl or haloalkyl, aryl, heteroaryl, optionally substituted allyl or optionally substituted arylmethyl, where $R^{13}$ is hydrogen, $C_1$ to $C_6$ alkyl or haloalkyl, aryl, heteroaryl, optionally substituted allyl or optionally substituted arylmethyl;

R⁷ is hydrogen, $C_1$ to $C_6$ alkyl or haloalkyl or heteroalkyl, aryl, arylmethyl, heteroaryl, COR¹², CO₂R¹², SO₂R¹², S(O)R¹² or CONR¹⁰R¹¹, where $R^{10-12}$ have the same definitions given above;

R⁸ and R⁹ are independently hydrogen, $C_1$ to $C_6$ alkyl or haloalkyl or heteroalkyl, optionally substituted $C_2$ to $C_6$ alkenyl or alkynyl, optionally substituted allyl, optionally substituted arylmethyl, optionally substituted aryl or optionally substituted heteroaryl;

X is OCH₂, SCH₂, NHCH₂, OC(O), SC(O), NHC(O), CH₂O, CH₂S, CH₂NH, C(O)O, C(O)S or C(O)NH;

Y is O, S or NR¹⁰, where $R^{10}$ has the same definition given above; and

Z is O, S, NR¹⁴, CR¹⁴R¹⁵, CR¹⁴R¹⁵CR¹⁶R¹⁷, OCR¹⁴R¹⁵, SCR¹⁴R¹⁵, CR¹⁴R¹⁵S, NR¹⁴CR¹⁵R¹⁶, or CR¹⁴R¹⁵NR¹⁶, where $R^{14}$ through $R^{17}$ each independently are hydrogen, $C_1$ to $C_6$ alkyl or haloalkyl or heteroalkyl, optionally substituted $C_2$ to $C_6$ alkenyl or alkynyl, optionally substituted allyl, optionally substituted arylmethyl, optionally substituted aryl or optionally substituted heteroaryl;

or a pharmaceutically acceptable salt thereof.

In a preferred aspect, the present invention provides a pharmaceutical composition comprising an effective amount of an progesterone receptor modulating compound of formula I or formula II shown above wherein $R^{1-17}$, X, Y and Z all have the same definitions as given above.

In a further preferred aspect, the present invention comprises a method of modulating processes mediated by progesterone receptors comprising administering to a patient an effective amount of a compound of formula I or formula II shown above, wherein $R^{1-17}$, X, Y and Z all have the same definitions as those given above.

Any of the compounds of the present invention can be synthesized as pharmaceutically acceptable salts for incorporation into various pharmaceutical compositions. As used herein, pharmaceutically acceptable salts include, but are not limited to, hydrochloric, hydrobrornic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl) aminomethane. Additional pharmaceutically acceptable salts are known to those skilled in the art.

The PR agonist, partial agonist and antagonist compounds of the present invention are particularly useful for female hormone replacement therapy and as modulators of fertility (e.g., as contraceptives or contragestational agents), either alone or in conjunction with estrogen receptor modulators. The PR missing data are also used in the treatment of dysfunctional uterine bleeding, dysmnenorrhea, endometriosis, leionyomas (uterine fibroids), hot flashes, mood disorders, meningiomas as well as in various hormone-dependent cancers, including, without limitation, cancers of ovaries, breast, endometrium and prostate.

It will be understood by those skilled in the art that while the compounds of the present invention will typically be employed as a selective agonists, partial agonists or antagonists, that there may be instances where a compound with a mixed steroid receptor profile is preferred. For example, use of a PR agonist (e.g., progestin) in female contraception often leads to the undesired effects of increased water retention and acne flare-ups. In this instance, a compound that is primarily a PR agonist, but also displays some androgen receptor (AR) and mineralocorticoid receptor (MR) modulating activity, may prove useful. Specifically, the mixed MR effects would be useful to control water balance in the body, while the AR effects would help to control any acne flare-ups that occur.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative PR modulator compounds (i.e., agonists, partial agonists and antagonists) according to the present invention include: 7-fluoro-4,4-dimethyl-5H-chromeno[3,4-f-]-1,3-benzo[d]oxazin-2-one (Compound 14); 9-bromo-7-fluoro-4,4-dimethyl-5H-chromeno[3,4-f]-1,3-benzo[d] oxazin-2-one (Compound 20); 7-fluoro-9-formyl-4,4-dimethyl-5H-chromeno[3,4-f]-1,3-benzo[d]oxazin-2-one (Compound 24); 7-fluoro-9-hydroxyiminomethyl-4,4-dimethyl-5H-chromeno[3,4-f]-1,3-benzo[d]oxazin-2-one (Compound 25); 9-cyano-7-fluoro-4,4-dimethyl-5H-chromeno[3,4-f]-1,3-benzo[d]oxazin-2-one (Compound 26).

Compounds of the present invention, comprising classes of heterocyclic nitrogen compounds and their derivatives, can be obtained by routine chemical synthesis by those skilled in the art, for example, by modification of the heterocyclic nitrogen compounds disclosed or by a total synthesis approach.

The sequences of steps to synthesize the compounds of the present invention are shown below in the general schemes. In each of the Schemes the R groups (e.g., $R^1$, $R^2$, etc.) correspond to the specific substitution patterns noted in the Examples. However, it will be understood by those skilled in the art that other functionalities disclosed herein at the indicated positions of compounds of formulas I and II also comprise potential substituents for the analogous positions on the structures within the Schemes. In a further aspect, the present invention provides a novel process for the preparation of the compounds of the present invention.

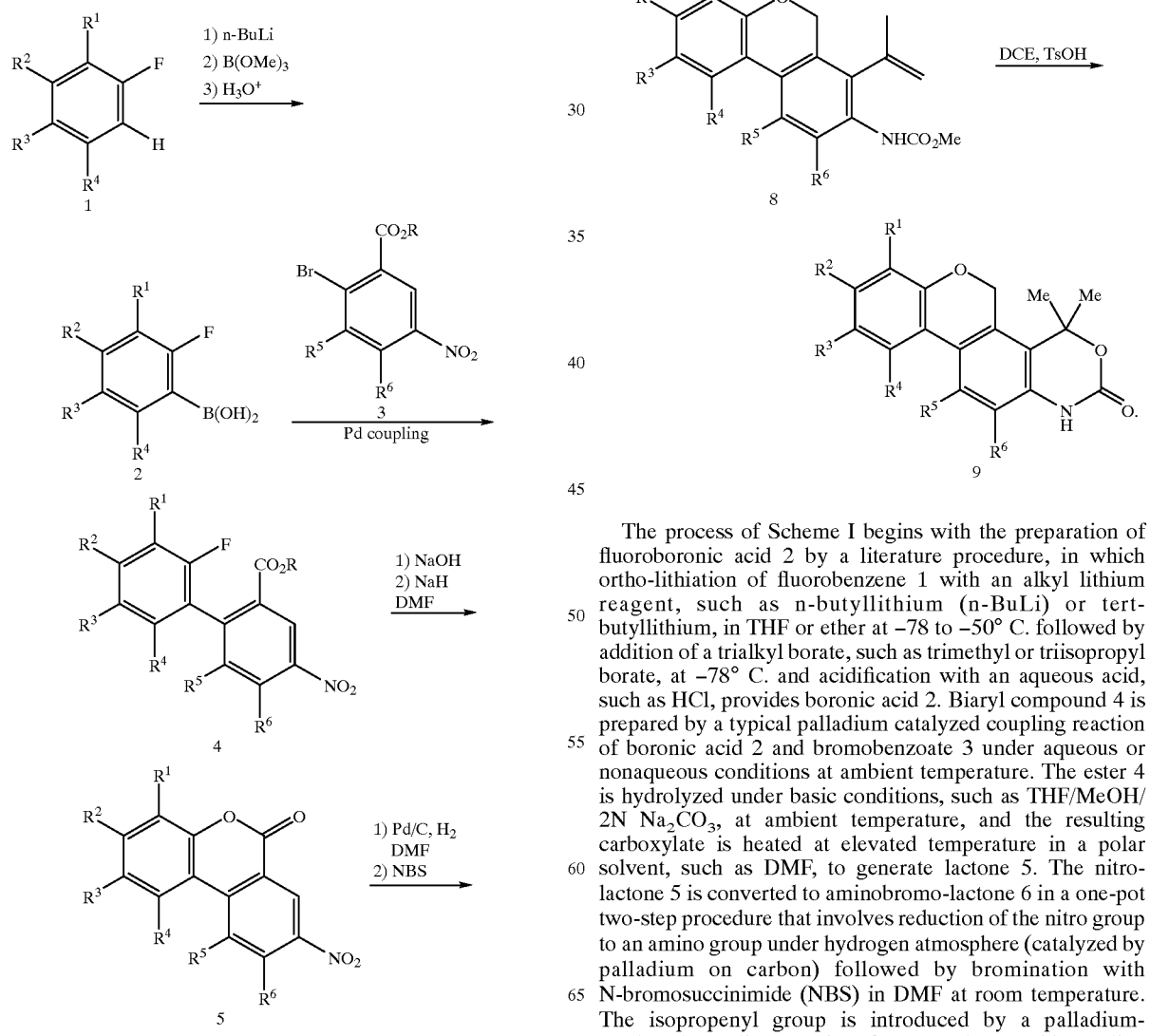

The process of Scheme I begins with the preparation of fluoroboronic acid 2 by a literature procedure, in which ortho-lithiation of fluorobenzene 1 with an alkyl lithium reagent, such as n-butyllithium (n-BuLi) or tert-butyllithium, in THF or ether at −78 to −50° C. followed by addition of a trialkyl borate, such as trimethyl or triisopropyl borate, at −78° C. and acidification with an aqueous acid, such as HCl, provides boronic acid 2. Biaryl compound 4 is prepared by a typical palladium catalyzed coupling reaction of boronic acid 2 and bromobenzoate 3 under aqueous or nonaqueous conditions at ambient temperature. The ester 4 is hydrolyzed under basic conditions, such as THF/MeOH/ 2N $Na_2CO_3$, at ambient temperature, and the resulting carboxylate is heated at elevated temperature in a polar solvent, such as DMF, to generate lactone 5. The nitro-lactone 5 is converted to aminobromo-lactone 6 in a one-pot two-step procedure that involves reduction of the nitro group to an amino group under hydrogen atmosphere (catalyzed by palladium on carbon) followed by bromination with N-bromosuccinimide (NBS) in DMF at room temperature. The isopropenyl group is introduced by a palladium-catalyzed coupling reaction, for example, Suzuki coupling reaction between isopropenylboronic acid and bromo compound 6. The resulting amino compound is then converted to the carbamate 7 by treatment with methyl chloroformate in the presence of 4-dimethylaminopyridine. Removal of the carbonyl group of lactone 7 is completed by stepwise reduction with typical reducing agents such as LiAlH$_4$ and Et$_3$SiH in the presence of a catalytic amount of acid (e.g., TFA) to afford compound 8. The final product 9 is obtained by the treatment of compound 8 with tosic acid (TsOH, p-toluenesulfonic acid) in refluxing dichloroethane (DCE).

conversions such as converting bromo to aldehyde by metal-halogen exchange followed by nucleophilic addition to DMF, or converting an aldehyde to an oxime by hydroxylamine treatment of the aldehyde, or converting an oxime to a cyano group by treatment of the oxime with thionyl chloride.

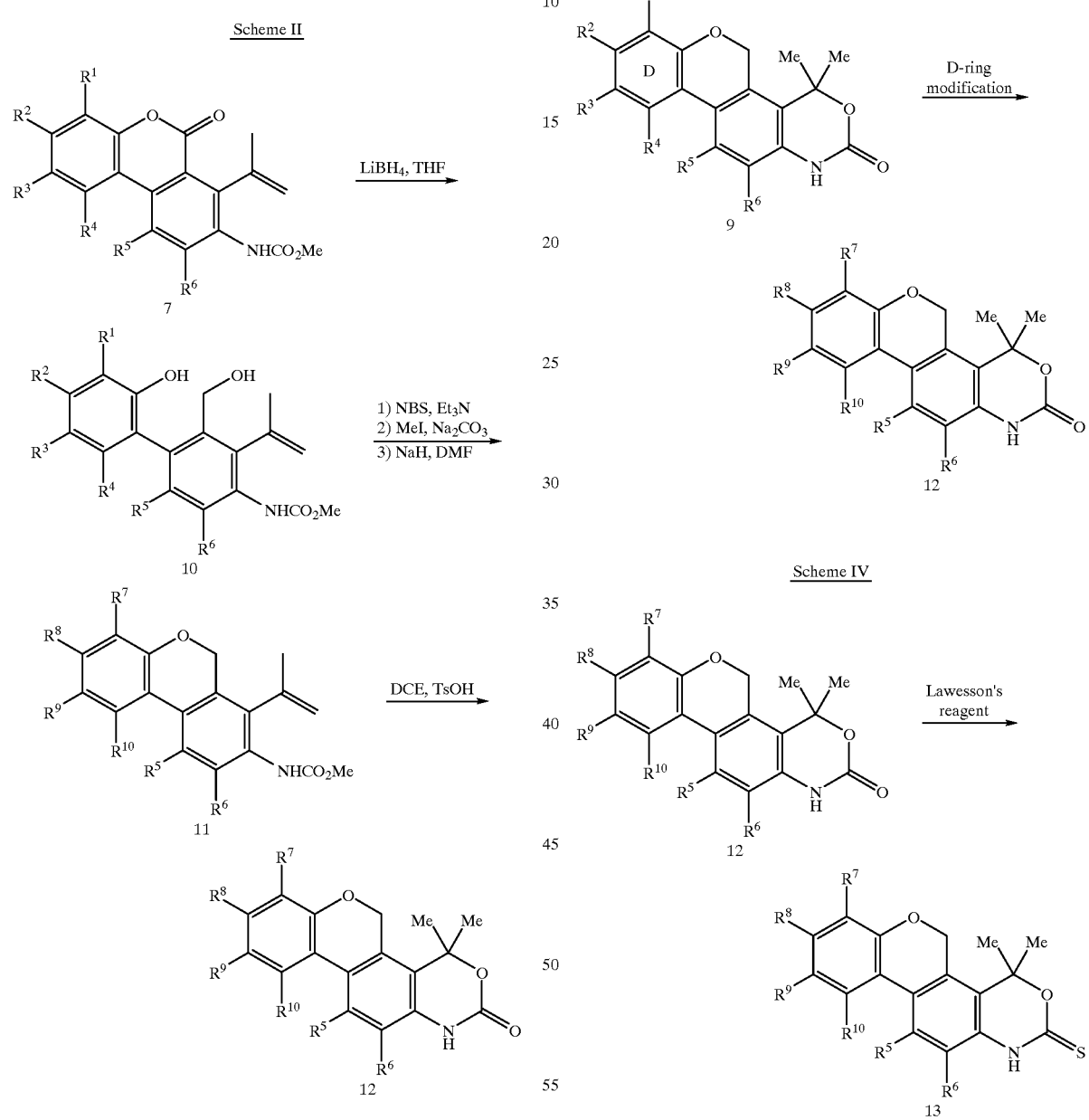

Scheme II describes a four-step, selective D-ring modification procedure, in which reduction of lactone 7 with a reducing agent such as LiBH$_4$ provides diol 10 and then NBS bromination of diol 10 in the presence of a base such as triethylamine followed by a selective methylation and NaH mediated nucleophllic cyclization in DMF affords compound 11. Treatment of compound 11 with more than one equivalent of an acid such as TsOH in refluxing dichloroethane provides compound 12.

Scheme III involves selective D-ring functional group conversion from $R^{1-4}$ to $R^{7-10}$ by known substituent group Scheme IV describes the conversion of compound 12 to its cyclic thiocarbamate analogue 13 by Lawesson's reagent (p-methoxyphenylthionophosphine sulfide dimer).

It will be understood by those skilled in the art that certain modifications can be made to the above-described methods that remain within the scope of the present invention.

The compounds of the present invention also include racemates, stereoisomers and mixtures of said compounds, including isotopically-labeled and radio-labeled compounds. Such isomers can be isolated by standard resolution techniques, including fractional crystallization and chiral colulmn chromatography.

As noted above, any of the PR modulator compounds of the present invention can be combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson), hydrophilic ointment (USP), and Lubriderm™ (Warner-Lambert).

The pharmaceutical compositions and compounds of the present invention will generally be administered in the form of a dosage unit (e.g., tablet, capsule etc.) at from about 1 $\mu$g/kg of body weight to about 500 mg/kg of body weight, more preferably from about 10 $\mu$g/kg to about 250 mg/kg, and most preferably from about 20 $\mu$g/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when radio- or isotopically-labeled as ligands for use in assays to determine the presence of PR in a cell background or extract. They are particularly useful due to their ability to selectively activate progesterone receptors, and can therefore be used to determine the presence of such receptors in the presence of other steroid receptors or related intracellular receptors.

Due to the selective specificity of the compounds of this invention for steroid receptors, these compounds can be used to purify samples of steroid receptors in vitro. Such purification can be carried out by mixing samples containing steroid receptors with one or more of the compounds of the present invention so that the compounds bind to the receptors of choice, and then separating out the bound ligand/receptor combination by separation techniques that are known to those of skill in the art. These techniques include column separation, filtration, centrifugation, tagging and physical separation, and antibody complexing, among others.

The compounds and pharmaceutical compositions of the present invention possess a number of advantages over previously identified steroid modulator compounds. For example, the compounds are extremely potent activators of PR, preferably displaying 50% maximal activation of PR at a concentration of less than 100 nM, more preferably at a concentration of less than 50 nM, more preferably yet at a concentration of less than 20 nM or less. Also, the selective compounds of the present invention generally do not display undesired cross-reactivity with other steroid receptors, as is seen with the compound mifepristone (RU486; Roussel Uclaf), a known PR antagonist that displays an undesirable cross reactivity on GR, thereby limiting its use in long-term, chronic administration. In addition, the compounds of the present invention, as small organic molecules, are easier to synthesize, provide greater stability and can be more easily administered in oral dosage forms than other known steroidal compounds.

The invention will be further illustrated by reference to the following non-limiting Examples.

EXAMPLE 1

7-Fluoro-4,4dimethyl-5H-chromeno[3,4-f]-1,3-benzo[d] oxazin-2-one (Compound 14; Structure 9 of Scheme I, Where $R^1$=fluoro, $R^{2-6}$=H)

2,3-Difluoroboronic Acid (Structure 2 of Scheme I, Where $R^1$=fluoro, $R^{2-4}$=H)

To a 500 mL flask charged with a solution of 1,2-difluorobenzene (15 g, 0.13 mmol) in THF (150 mL) at –78° C. was added dropwise n-BuLi (7.0 M in hexane, 19 mL, 0.13 mol). The reaction mixture was stirred at –78° C. for 2.5 hours and then a solution of trimethylborate (30 mL, 0.26 mol. 2.0 equiv) in THF (90 mL) previously cooled to –78° C. was added, after which the mixture was allowed to warm up to room temperature overnight. Next the reaction mixture was acidified to pH~1 using HCl (3 N aqueous) and then stirred for 15 minutes. Then the mixture was extracted with ether (2×300 mL), washed with water (150 mL) and dried over $Na_2SO_4$. The solvent was removed in vacuo to yield 20 g (96%) of 2,3-difluoroboronic acid as a white solid. Data for 2,3-difluoroboronic acid: rf=0.39 (EtOAc:hexanes, 3:7).

Methyl 2-(2,3-Difluorophenyl)-5-nitrobenzoate (Compound 15; Structure 4 of Scheme I, Where $R^1$=fluoro, $R^{2-6}$=H)

A mixture of 2,3-difluoroboronic acid (20 g, 0.12 mol. 1.3 equiv), methyl 2-bromo-5-nitrobenzoate (25 g, 96 mmol) (Structure 3, where R=methyl, $R^{5-6}$=H), tetrakis(triphenylphosphine)palladium(0) (3.6 g, 3.1 mmol, 3.2% equiv) and aqueous sodium carbonate (2 M, 200 mL) in toluene (200 mL) and ethanol (100 mL) was heated at reflux overnight until completion of the reaction was indicated by TLC. The reaction mixture was extracted with EtOAc (2×400 mL), washed with brine (300 mL) and dried over $Na_2SO_4$. Removal of solvent provided a brown solid, which was recrystallized from i-PrOH:hexanes to give Compound 15 (22.8 g, 83%) as a white solid. Data for 15: rf=0.32 ($CH_2Cl_2$:hexanes, 4:6); $^1$H NMR (400 MHz, $CDCl_3$) $\delta$5 8.87 (d, J=1.2, 1), 8.43 (dd, J=8.3 and 1.2, 1), 7.58 (d, J=8.6, 1), 7.29–7.17 (m, 2), 7.10–7.02 (m, 1) and 3.82 (s, 3H).

4-Fluoro-8-nitro-6H-dibenzo[b,d]pyran-6-one (Compound 16; Structure 5 of Scheme I, Where $R^1$=fluoro, $R^{2-6}$=H)

To a solution of Compound 15 (20 g, 69 mmol) in THF:MeOH (~2.5:1) (370 mL) was added 10% aqueous NaOH (82 mL), and the reaction mixture was stirred at room temperature for 1 hour. The mixture was concentrated, acidified to pH~1using 3N HCl and then extracted with EtOAc (2×400 mL). The combined extracts were washed with brine, dried over $Na_2SO_4$ and concentrated to afford the acid as an off-white solid. To a solution of the crude acid in dry DMF (180 mL) was added NaH (4.0 g, 1.5 equiv), and the mixture was heated at ~80° C. for 2 hours, at which time TLC indicated completion of the reaction. The reaction mixture was concentrated under reduced pressure to a small volume, and then water (5 mL) was added. The mixture was cooled to −15° C. to afford a white precipitate, which was filtered and washed with cold water and hexane to give Compound 16 (17 g, 95%). Data for 16: rf=0.36 (EtOAc:hexanes, 3:7); $^1$H NMR (400 MHz, CDCl$_3$) δ9.28 (d, J=1.1, 1), 8.68 (dd, J=8.5 and 1.1, 1), 8.32 (d, J=8.5, 1), 7.91 (d, J=8.0, 1) and 7.46–7.36 (m, 2).

8-Amino-7-bromo-4-fluoro-6H-dibenzo[b,d]pyran-6-one (Compound 17; Structure 6 of Scheme I, Where R$^1$=fluoro, R$^{2-6}$=H)

A mixture of Compound 16 (8.8 g, 34 mmol) and 10% Pd/C (0.95 g, 2.5% equiv.) in DMF (150 mL) in a Parr apparatus was shaken at room temperature under H$_2$ (40–60 psi) overnight until completion of the hydrogenation was indicated by TLC. The reaction mixture was then carefully passed through filter paper to remove all traces of Pd/C catalyst. NBS (6.0 g, 34 mmol) was added to the filtrate, and the resulting mixture was stirred at room temperature for 2–3 hours. The mixture was concentrated under reduced pressure, and then water was added to initiate precipitation. The solid was filtered and washed with cold water to afford Compound 17 (8.6 g, 83%) as a pale brown solid. Data for 17: rf=0.11 (EtOAc:hexanes, 1:3); $^1$H NMR (400 MHz, DMSO-d$_6$) δ8.20 (d, J=8.8, 1), 7.97 (d, J=8.0, 1), 7.38 (d, J=8.8, 1), 7.35–7.27 (m, 2), 6.24 (s, 2).

4-Fluoro-7-isopropenyl-8-methoxycarbonylamino-6H-dibenzo[b,d]pyran-6-one (Compound 18; Structure 7 of Scheme I, Where R$^1$=fluoro, R$^{2-6}$=H)

To a solution of 2-bromopropene (1.2 g, 10 mmol) in THF (25 mL) at −78° C. was added t-BuLi (1.7 M in pentane, 12 mL, 20 mmol), and the resulting yellow solution was stirred for 10 minutes. Trimethylborate (3.0 mL, 26 mmol) was added via syringe, and the reaction mixture was warmed up slowly overnight to yield a white slurry. The reaction mixture was acidified to pH~2, stirred at room temperature for 1 hour, extracted with EtOAc (2×50 mL), washed with brine and then was concentrated to afford the crude boronic acid as a white solid.

A mixture of this crude boronic acid, Compound 17 (1.5 g, 4.8 mmol), K$_2$CO$_3$ (2.8 g, 20 mmol) and Pd(PPh$_3$)$_4$ (0.10 g, 0.087 mmol, 1.8% equiv) in toluene (45 mL), EtOH (45 mL) and water (20 mL) was heated at reflux for 2 hours. The dark reaction mixture was acidified to pH~2 and extracted with EtOAc (2×150 mL). Removal of solvent provided a crude dark solid that contained 8-amino-4-fluoro-7-isopropenyl-6H-dibenzo(b,d)pyran-6-one. To the crude mixture in THF (40 mL) at room temperature was added ClCO$_2$Me (1.7 mL, 20 mmol) and DMAP (0.53 g, 4.3 mmol), and the resulting cloudy solution was stirred at room temperature for 5 hours. The reaction was quenched with water (50 mL), and the reaction mixture was extracted with EtOAc and washed with aqueous Na$_2$CO$_3$, NH$_4$Cl and brine. Removal of solvent and chromatography of the crude mixture afforded Compound 18 (0.35 g, 26%) as a pale yellow solid. Data for 18: rf=0.34 (EtOAc:Hexane, 1:3); $^1$H NMR (400 MHZ, CDCl$_3$) δ8.72 (d, J=8.9, 1), 8.08 (d, J=9.0, 1), 7.79 (bd, J=6.5, 1), 7.54 (s, 1), 7.24–7.18 (m, 2), 5.52 (s, 1), 4.95 (s, 1), 3.81 (s, 3) and 2.14 (s, 3).

4-Fluoro-7-isoproperly-8-methoxycarbonylamino-6H-dibenzo[b,d]pyran (Compound 19; Structure 8 of Scheme I, Where R$^1$=fluoro, R$^{2-6}$=H)

To a solution of Compound 18 (70 mg, 0.21 mmol) in THF (8 mL) was added LiAlH$_4$ (8.0 mg, 0.21 mmol), and the resulting mixture was stirred at room temperature for 30 minutes. The reaction was quenched with water, and the reaction mixture was extracted with EtOAc and concentrated. Chromatography afforded 4-fluoro-6-hydroxy-7-isopropenyl-8-methoxycarbonylamino-6H-dibenzo[b,d]pyran (20 mg, 28%) as a yellow solid, which was treated with a catalytic amount of TFA in the presence of Et$_3$SiH (0.2 mL) and CH$_2$Cl$_2$ (4 mL) for 2 hours at room temperature. Purification provided Compound 19 (13 mg, 68%) as a solid. Data for 19: $^1$H NMR (400 MHz, CDCl$_3$) δ8.13 (d, J=8.2, 1), 7.61 (d, J=8.6, 1), 7.46 (d, J=7.5, 1), 7.04–6.93 (m, 2), 6.89 (s, 1), 5.55 (s, 1), 5.10 (d,J=13.5, 1), 5.07 (d, J=13.5, 1), 5.03 (s, 1), 3.79 (s, 3) and 2.01 (s, 3).

7-Fluoro-4,4-dimethyl-5H-chromeno[3,4-f]-1,3-benzo[d]oxazin-2-one (Compound 14; Structure 9 of Scheme I, Where R$^1$=fluoro, R$^{2-6}$=H)

A mixture of Compound 19 (13 mg, 0.041 mmol) and TsOH (16 mg, 0.084 mmol) in dichloroethane (5 mL) was heated at reflux for 15 hours and concentrated. The mixture was diluted in EtOAc (20 mL) and was washed with aqueous Na$_2$CO$_3$ (2×5 mL) and brine. Removal of solvent provided the product as a white solid, which was recrystallized from EtOAc:hexanes to yield 6 mg (49%) of Compound 14 as a white solid. Data for 14: rf=0.23 (EtOAc:hexanes, 1:1); $^1$H NMR (400 MHz, CDCl$_3$) δ8.71 (bs, 1), 7.58 (d, J=8.4, 1), 7.40 (d, J=7.4, 1), 7.08–6.95 (m, 2), 6.88 (d, J=8.4, 1), 5.24 (s, 2) and 1.84 (s, 6).

EXAMPLE 2

9-Bromo-7-fluoro-4,4dimethyl-5H-chromeno[3,4-f]-1,3-benzo[d]oxazin-2-one (Compound 20; Structure 12 of Scheme II, Where R$^7$=fluoro, R$^9$=bromo, R$^{5-6}$=R$^8$=R$^{10}$=H)

N-Methoxycarbonyl-3-hydroxymethyl-4-(3-fluoro-2-hydroxyphenyl)-2-isopropenylaniline (Compound 21; Structure 10 of Scheme II, Where R$^1$=fluoro, R$^{2-6}$=H)

To a solution of Compound 18 (Structure 7 of Scheme II, where R$^1$=fluoro, R$^{2-6}$=H) (0.33 g, 1.0 mmol) in THF (30 mL) was added LiAlH$_4$ (44 mg, 2.0 mmol) portionwise at room temperature, and the resulting mixture was stirred at room temperature for 2 hours. The reaction was quenched with water, and the reaction mixture was extracted with EtOAc. Removal of solvent followed by chromatography afforded Compound 21 (0.30 g, 96%) as a colorless oil. Data for 21: rf=0.11 (EtOAc:hexanes, 1:3); $^1$H NMR (400 MHz, CDCl$_3$) showed a mixture of rotomers.

N-Methoxycarbonyl-3-hydroxymethyl-4-(5-bromo-3-fluoro-2-hydroxyphenyl)-2-isopropenylaniline (Compound 22: Structure 10 of Scheme II, Where R$^1$=fluoro, R$^3$=bromo, R$^2$=R$^{4-6}$=H)

NBS (0.18 g, 1.0 mmol) was added to a mixture of Compound 21 (0.30 g, 0.96 mmol) and Et$_3$N (1.0 mL) in CH$_2$Cl$_2$ (12 mL) at room temperature. After 10 minutes, the mixture was diluted with EtOAc (50 mL), and washed with water, aqueous NH$_4$Cl and brine. Removal of solvent and chromatography of the residue provided 0.34 g (86%) of Compound 22 as a yellow oil. Data for 22: rf=0.12 (EtOAc:hexanes, 1:3).

2-Bromo-4-fluoro-7-isopropenyl-8-methoxycarbonylamino-6H-dibenzo[b,d]pyran (Compound 23: Structure 11 of Scheme II, Where R$^7$=fluoro, R$^9$=bromo, R$^{5-6}$=R$^8$=R$^{10}$=H)

To a solution of Compound 22 (0.34 g, 0.83 mmol) in DMF (10 mL) was added K$_2$CO$_3$ (0.14 g, 1.0 mmol) and MeI (0.5 mL, excess), and the mixture was stirred at room temperature for 1 hour. Standard work-up followed by chromatography afforded 0.28 g (78%) of N-methoxycarbonyl-2-isopropenyl-3-hydroxymethyl-4-(5-bromo-3-fluoro-2-methoxyphenyl)aniline. Data for the methylated intermediate: rf=0.52 (EtOAc:hexanes, 1:1); $^1$H NMR (400 MHz, CDCl$_3$) (rotomers) δ8.13/8.02 (bs, 1), 7.30 (m, 1), 7.17–6.95 (m, 3), 5.61/5.53 (s, 1), 5.21/4.97 (s, 1), 4.50–4.12 (m, 2), 3.79/2.95 (s, 3), 3.62/2.88 (s, 3) and 2.20/2.02 (s, 3).

A mixture of the methylated intermediate (0.28 g, 0.65 mmol) and NaH (30 mg, 0.75 mmol) in DMF (10 mL) was heated in an 80° C. oil bath for 2 hours until the reaction went to completion. Standard work-up followed by chromatography afforded 0.20 g (80%) of Compound 23 as a solid. Data for 23: rf=0.65 (EtOAc:hexanes, 1:1); $^1$H NMR (400 MHz, CDCl$_3$) δ8.15 (d, J=8.7, 1), 7.58 (m, 1), 7.56 (d, J=8.7, 1), 7.15 (dd, J=9.5 and 2.0, 1), 6.89 (s, 1), 5.56 (s, 1), 5.09 (d, J=12, 1), 5.07 (d, J=12, 1), 5.03 (s, 1), 3.79 (s, 3) and 2.00 (s, 3).

9-Bromo-7-fluoro-4,4-dimethyl-5H-chromeno[3,4-f]-1,3-benzo[d]oxazin-2-one (Compound 20; Structure 12 of Scheme II, Where $R^7$=fluoro, $R^9$=bromo, $R^{5-6}$=$R^8$=$R^{10}$=H)

A mixture of Compound 23 (0.12 g, 0.31 mmol) and TsOH (0.12 g, 0.62 mmol) in dichloroethane (15 mL) was heated at reflux for 15 hours and concentrated. The mixture was diluted in EtOAc (50 mL) and then washed with aqueous Na$_2$CO$_3$ (2×10 mL) and brine. Removal of solvent provided the product as a white solid, which was recrystallized from EtOAc:hexanes to give 60 mg (49%) of Compound 20. Data for 20: rf=0.30 (EtOAc:hexanes, 1:1); $^1$H NMR (400 MHz, CDCl$_3$) δ8.09 (s, 1), 7.53 (d, J=8.3, 1), 7.52 (m, 1), 7.19 (dd, J=9.4 and 1.9, 1), 5.22 (s, 2) and 1.82 (s, 6). Some starting material was also recovered (55 mg, 45%).

EXAMPLE 3

7-Fluoro-9-formyl-4,4dimethyl-5H-chromeno[3,4-f]-1,3-benzo[d]oxazin-2-one (Compound 24; Structure 12 of Scheme III, Where $R^7$=fluoro, $R^9$=formyl, $R^{5-6}$=$R^8$=$R^{10}$=H)

MeLi (1.4 M in ether, 0.10 mL, 0.14 mmol) was added to a −70° C. solution of Compound 20 (50 mg, 0.13 mmol) in THF (12 mL), and the resulting mixture was stirred for 10 minutes before n-BuLi (1.6 M in hexane, 0.10 mL, 0.16 mmol) was added. The reaction mixture was warmed up to −40° C. and then cooled back down to −70° C. DMF (0.40 mL, 5.0 mmol) was added to the reaction mixture, which was then warmed to room temperature, quenched with water (10 mL) and extracted with EtOAc (2×20 mL). Chromatography afforded 26 mg (61%) of Compound 24 as a white solid. Data for 24: rf=0.13 (EtOAc:hexanes, 1:1); $^1$H NMR (400 MHz, CDCl$_3$) δ9.97 (d, J=1.8, 1), 9.33 (bs, 1), 8.19 (t, J=1.3, 1), 7.90 (d, J=8.4, 1), 7.61 (dd, J=10.3 and 1.3, 1), 7.15 (d, J=8.4, 1), 5.51 (s, 2) and 1.83 (s, 6).

EXAMPLE 4

7-Fluoro-9-hydroxyiminomethyl-4,4dimethyl5H-chromeno[3,4-f]-1,3-benzo[d]oxazin-2-one (Compound 25: Structure 12 of Scheme III, Where $R^7$=fluoro, $R^9$=hydroxyiminomethyl, $R^{5-6}$=$R^8$=$R^{10}$=H)

NH$_2$OH-HCl (10 mg, 0.14 mmol) and pyridine (0.1 mL, 1.4 mmol) were added to a solution of Compound 24 (20 mg, 0.061 mmol) in ethanol (4 mL), and the resulting mixture was stirred at room temperature for 1 hour. The reaction mixture was concentrated, dissolved in EtOAc (30 mL), washed with water and brine, and re-concentrated to afford 18 mg (86%) of Compound 25 as a white solid. Data for 25: rf=0.11 (EtOAc:hexanes, 1:1); $^1$H NMR (400 MHz, acetone-d$_6$) δ9.27 (s, 1), 8.15 (s, 1), 7.80 (s, 1), 7.78 (d, J=8.3, 1), 9.39 (d, J=11.2, 1), 7.11 (d, J=8.3, 1), 5.39 (s, 2) and 1.81 (s, 6).

EXAMPLE 5

9-Cyano-7-fluoro-4,4dimethyl-5H-chromeno[3,4-f]-1,3-benzo[d]oxazin-2one (Compound 26: Structure 12 of Scheme III, Where $R^7$=fluoro, $R^9$=cyano, $R^{5-6}$=$R^8$=$R^{10}$=H)

Compound 25 (10 mg, 0.029 mmol) was treated with thionyl chloride (0.032 mL, 0.043 mmol) in dichloromethane (10 mL) at room temperature for 40 minutes. The reaction mixture was then quenched with a saturated Na$_2$CO$_3$ solution (2 mL), extracted with EtOAc (2×20 mL) and washed with brine. Removal of solvent followed by chromatography afforded 8 mg (90%) of Compound 26 as a white solid. Data for 26: rf=0.32 (EtOAc:hexanes, 1:1); $^1$H NMR (400 MHz, acetone-d$_6$) δ9.35 (bs, 1), 8.05 (t, J=1.5, 1 H), 7.90 (d, J=8.4, 1), 7.59 (dd, J=10.6 and 1.5, 1), 7.15 (d, J=8.4, 1), 5.51 (s,2 H) and 1.82 (s, 6).

Steroid Receptor Activity

Utilizing the cotransfection assay described by R. M. Evans, *Science,* 240 (1988) 889–895, the disclosure of which is herein incorporated by reference, the compounds of the present invention were tested and found to have strong, specific activity as agonists, partial agonists and antagonists of PR. This assay is described in further detail in the following U.S. Patents, the disclosures of which are incorporated herein by reference: "Retinoic Acid Receptor Method", R. M. Evans, E. Ong, P. S. Segui, C. C. Thompson, K. Umesono, V. Giguere, U.S. Pat. No. 4,981,784; and "Hormone Receptor-Related Assays", R. M. Evans, C. A. Weinberger, S. M. Hollenberg, V. Giguere, J. Arriza, C. C. Thompson, E. S. Ong, U.S. Pat. No. 5,071,773.

The cotransfection assay provides a method for identifying functional agonists and partial agonists that mimic, or antagonists that inhibit, the effect of native hormones, and for quantifying their activity for responsive intracellular receptor (IR) proteins. In this regard, the cotransfection assay mimics an in vivo system in the laboratory. Importantly, activity in the cotransfection assay correlates very well with known in vivo activity, such that the cotransfection assay functions as a qualitative and quantitative predictor of a tested compound's in vivo pharmacology. See, for example, "Interaction of Glucocorticoid Analogues with the Human Glucocorticoid Receptor", T. S. Berger, Z. Parandoosh, B. W. Perry and R. B. Stein, *J. Steroid Biochem. Molec. Biol.,* 41 (1992) 733–738 (hereinafter "Berger"), the disclosure of which is herein incorporated by reference.

In the cotransfection assay, a cloned cDNA for an IR (e.g., human PR, AR or GR) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (cotransfected) into the same cells in conjunction with the IR gene. This second gene, comprising the cDNA for a reporter protein, such as firefly luciferase (LUC), is controlled by an appropriate hormone responsive promoter containing a hormone response element (HRE). This reporter plasmid functions as a reporter for the transcription-modulating activity of the target IR. Thus, the reporter acts as a surrogate for the products (mRNA, then protein) normally expressed by a gene under control of the target receptor and its native hormone.

The cotransfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the cotransfection assay is carried out in the presence of a constant concentration of an agonist to the target IR (e.g., progesterone for PR) known to induce a defined reporter signal.

Increasing concentrations of a suspected antagonist will decrease the reporter signal (e.g., luciferase production). The cotransfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activities of selected steroid receptor modulator compounds of the present invention were evaluated utilizing the cotransfection assay, and in standard IR binding assays, according to the following illustrative Examples.

EXAMPLE 6

Cotransfection Assay

The function and detailed preparation procedure of the cotransfection assays have been described previously. See, for example, "Nonsteroidal Human Progesterone Receptor Modulators from the Marine Alga *Cymopolia barbata*", C. Pathirana, R. B. Stein, T. S. Berger, W. Fenical, T. Ianiro, D. E. Mais, A Torres, M. E. Goldman, *Mol Pharm.*, 47 (1995) 630–635 (hereinafter "Pathirana"). Briefly, the cotransfection assays were carried out in CV-1 cells (African green monkey kidney fibroblasts) that had been transiently transfected, using the standard calcium phosphate coprecipitation procedure (see, e.g., Berger), with plasmid containing receptor, MTV-LUC reporter, pRS-β-Gal and filler DNA (Rous sarcoma virus chloramphenical acetyltransferase). The agonist activity was determined by examining the LUC expression (normalized response), and the efficacy readout was a relative value to the maxima LUC expression produced by a reference agonist, e.g., progesterone for hMR, dihydrotestosterone (DHT) for hAR, dexamethasone for hGR, aldosterone for hMR, estradiol for hER. All the cotransfection experiments were carried out in 96-well plates by automation (Beckman Biomomek automated workstation).

Receptor Binding Assays

The preparation of receptor binding assays for hPR-A, hGR, and AR has been described (see, e.g., Pathirana).

The agonist, antagonist and binding activity assay results of selected progesterone receptor modulator compounds of the present invention and the standard reference compounds on PR, as well as the cross-reactivity of selected compounds on the AR, ER, MR and GR receptors, are shown in Tables 1–2 below. Efficacy is reported as the percent maximal response observed for each compound relative to the reference agonist and antagonist compounds indicated above. Also reported in Tables 1–2 for each compound is its antagonist potency or $IC_{50}$ (which is the concentration (nM), required to reduce the maximal response by 50%), its agonist potency or $EC_{50}$ (nM).

TABLE 1

Agonist, antagonist and binding activity of progesterone receptor modulator compounds of present invention and the reference agonist compound, progesterone (Prog), and reference antagonists compound, RU486 and ZK299.

| Cmpd No. | PR Agonist CV-1 Cells | | PR Antagonist CV-1 Cells | | PR Binding |
|---|---|---|---|---|---|
| | Efficacy (%) | Potency (nM) | Efficacy (%) | Potency (nM) | Ki (nM) |
| Prog | 100 | 2.9 | na | na | 3.5 |
| RU486 | na | na | 96 | 0.18 | 0.58 |
| ZK299 | na | na | 99 | 1.6 | 18 |
| 14 | 30 | 2500 | 95 | 25 | 172 |
| 20 | 30 | 500 | 80 | 20 | 17 |
| 24 | na | na | 84 | 98 | 181 |
| 25 | 46 | 623 | 87 | 23 | 65 |
| 26 | 60 | 1000 | 68 | 16 | 20 | na = not active (i.e. efficacy of <20 and potency of >10,000)
nt = not tested

TABLE 2

Overall agonist and antagonist potency of selected progesterone receptor modulator compounds of present invention and the reference agonist and antagonist compounds shown in Table 1 on PR, AR, ER, GR and MR.

| Cmpd No. | PR Potency | | AR Potency | | ER Potency | | GR Potency Antag (nM) | MR Potency Antag (nM) |
|---|---|---|---|---|---|---|---|---|
| | Agon (nM) | Antag (nM) | Agon (nM) | Antag (nM) | Agon (nM) | Antag (nM) | | |
| 14 | 2500 | 25 | na | 200 | na | na | na | na |
| 20 | 500 | 20 | na | 1000 | na | na | na | na |
| 24 | na | 98 | na | 130 | na | na | na | na |
| 25 | 623 | 23 | na | 100 | na | na | na | na |
| 26 | 1000 | 16 | na | 300 | na | na | na | na |
| Prog | 3 | na | 1300 | na | na | na | na | nt |
| RU486 | no | 0.1 | no | 12 | no | 1500 | 0.7 | 1100 |
| DHT | na | 1800 | 6 | na | 1700 | na | na | nt |
| Flut | na | 1900 | na | 26 | na | na | na | na |
| Estr | nt | nt | na | na | 7 | na | na | nt |
| ICI 164 | na | na | na | na | na | 160 | na | na |
| Spir | nt | 268 | nt | nt | na | na | 2000 | 25 | na = not active (i.e., efficacy of >20 and potency of >10,000);
nt = not tested

Pharmacological and Other Applications

As will be discernible to those skilled in the art, the PR modulator compounds of the present invention can be readily utilized in pharmacological applications where PR antagonist or agonist activity is desired, and where it is desired to minimize cross reactivities with other steroid receptor related IRs. In vivo applications of the invention include administration of the disclosed compounds to mammalian subjects, and in particular to humans.

The following Example provides illustrative pharmaceutical composition formulations:

EXAMPLE 7

Hard gelatin capsules are prepared using the following ingredients:

|  | Quantity (mg/capsule) |
| --- | --- |
| COMPOUND 26 | 140 |
| Starch, dried | 100 |
| Magnesium stearate | 10 |
| Total (mg) | 250 |

The above ingredients are mixed and filled into hard gelatin capsules in 250 mg quantities.

A tablet is prepared using the ingredients below:

|  | Quantity (mg/tablet) |
| --- | --- |
| COMPOUND 26 | 140 |
| Cellulose, microcrystalline | 200 |
| Silicon dioxide, filmed | 10 |
| Stearic acid | 10 |
| Total (mg) | 360 |

The components are blended and compressed to form tablets each weighing 360 mg.

Tablets, each containing 60 mg of active ingredient, are made as follows:

|  | Quantity (mg/tablet) |
| --- | --- |
| COMPOUND 26 | 60.0 |
| Starch | 45.0 |
| Cellulose, microcrystalline | 35.0 |
| Polyvinylpyrrolidone (PVP) (as 10% solution in water) | 4.0 |
| Sodium carboxymethyl starch (SCMS) | 4.5 |
| Magnesium stearate | 0.5 |
| Talc | 1.0 |
| Total (mg) | 150.0 |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, and then added to the granules which, after mixing, are compressed on a tablet machine to yield tablets each weighing 150 mg.

Suppositories, each containing 225 mg of active ingredient, may be made as follows:

|  |  |
| --- | --- |
| COMPOUND 26 | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

|  |  |
| --- | --- |
| COMPOUND 26 | 100 mg |
| Isotonic saline | 1,000 mL |
| Glycerol | 100 mL |

The compound is dissolved in the glycerol and then the solution is slowly diluted with isotonic saline. The solution of the above ingredients is then administered intravenously at a rate of 1 mL per minute to a patient.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A compound having the formula:

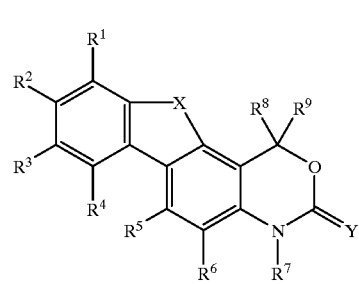

(I)

wherein:

$R^1$ through $R^6$ are independently hydrogen, F, Cl, Br, I, $NO_2$, CN, $OR^{10}$, $NR^{10}R^{11}$, $SR^{10}$, $COR^{12}$, $CO_2R^{12}$, $CONR^{10}R^{11}$, optionally substituted $C_1$ to $C_6$ alkyl or heteroalkyl, $C_1$ to $C_6$ haloalkyl, optionally substituted $C_3$ to $C_8$ cycloalkyl, optionally substituted $C_2$ to $C_6$ alkenyl or alkynyl, optionally substituted allyl, optionally substituted aryl or heteroaryl, or optionally substituted arylmethyl, where $R^{10}$ and $R^{11}$ are independently hydrogen, $C_1$ to $C_6$ alkyl or heteroalkyl or haloalkyl, aryl, heteroaryl, optionally substituted allyl, optionally substituted arylmethyl, $COR^{13}$, $SO_2R^{13}$ or $S(O)R^{13}$, where $R^{12}$ is hydrogen, $C_1$ to $C_6$ alkyl or heteroalkyl or haloalkyl, aryl, heteroaryl, optionally substituted allyl or optionally substituted arylmethyl, where $R^{13}$ is hydrogen, $C_1$ to $C_6$ alkyl or haloalkyl, aryl, heteroaryl, optionally substituted allyl or optionally substituted arylmethyl;

$R^7$ is hydrogen, $C_1$ to $C_6$ alkyl or haloalkyl or heteroalkyl, aryl, arylmethyl, heteroaryl, $COR^{12}$, $CO_2R^{12}$, $SO_2R^{12}$, $S(O)R^{12}$ or $CONR^{10}R^{11}$, where $R^{10}$ to $R^{12}$ have the same definitions given above;

$R^8$ and $R^9$ are independently hydrogen, $C_1$ to $C_6$ alkyl or haloalkyl or heteroalkyl, optionally substituted $C_2$ to $C_6$ alkenyl or alkynyl, optionally substituted allyl, optionally substituted arylmethyl, optionally substituted aryl or optionally substituted heteroaryl;

X is $OCH_2$, $SCH_2$, $NHCH_2$, OC(O), SC(O), NHC(O), $CH_2O$, $CH_2S$, $CH_2NH$, C(O)O, C(O)S or C(O)NH;

Y is O, S or $NR^{10}$, where $R^{10}$ has the same definition given above;

or a pharmaceutically acceptable salt thereof.

2. A compound of claim 1, or a pharmaceutically acceptable salt thereof, selected from the group consisting of: 7-fluoro-4,4-dimethyl-5H-chromeno(3,4-f)-1,3-benzo(d)oxazin-2-one; 9-bromo-7-fluoro-4,4-dimethyl-5H-chromeno(3,4-f)-1,3-benzo(d)oxazin-2-one; 7-fluoro-9-formyl-4,4-dimethyl-5H-chromeno(3,4-f)-1,3-benzo(d)oxazin-2-one; 7-fluoro-9-hydroxyiminomethyl-4,4-dimethyl-5H-chromeno(3,4-f)-1,3-benzo(d)oxazin-2-one; and 9-cyano-7-fluoro-4,4-dimethyl-5H-chromeno(3,4-f)-1,3-benzo(d)oxazin-2-one.

3. A pharmaceutical composition comprising, in a pharmaceutically acceptable vehicle suitable for enteral, parenteral, or topical administration, one or more compounds as claimed in claim 1.

4. A compound of claim 1 wherein said compound modulates a process mediated by one or more steroid receptors from the group consisting of progesterone receptors and androgen receptors.

5. A compound of claim 1, wherein said compound modulates female hormone responsive diseases.

6. A compound of claim 1 wherein said compound modulates male hormone responsive diseases.

7. A method of using a compound of claim 1 to treat a hormone responsive disease wherein the compound is administered in combination with a progesterone receptor agonist, an estrogen receptor agonist, or both.

8. A method of inducing contraception in a mammal, the method comprising administering to a mammal in need thereof a pharmaceutically effective amount of a compound of claim 1 or a pharmaceutically acceptable salt thereof.

9. A method of treatment in a mammal of carcinomas or adenocarcinomas of the endometrium, ovary, breast, colon or prostate, the method comprising administering to a mammal in need thereof a pharmaceutically effective amount of a compound of claim 1, or a pharmaceutically acceptable salt thereof.

10. A method of treating benign or malignant neoplastic disease in a mammal, the method comprising administering to a mammal in need thereof a pharmaceutically effective amount of a compound of claim 1 or a pharmaceutically acceptable salt;

wherein said disease is selected from the group consisting of uterine fibroids, endometriosis, benign prostatic hypertrophy, carcinomas and adenocarcinomas of the endometrium, ovary, breast, colon, prostate or pituitary, meningioma, and other hormone-dependent tumors.

* * * * *

UNITED STATES PATENT AND TRADEMARK OFFICE
CERTIFICATE OF CORRECTION

PATENT NO.    : 6,358,947 B1
DATED         : March 19, 2002
INVENTOR(S)   : L. Zhi et al.

It is certified that error appears in the above-identified patent and that said Letters Patent is hereby corrected as shown below:

Column 1,
Line 47, replace "D. T. Winr," with -- D.T. Winn --.

Column 2,
Line 28, replace "hereof However," with -- hereof. However, --.
Line 62, replace "mnore" with -- more --.

Column 4,
Line 10, replace "ofthe" with -- of the --.
Line 29, replace "missing data" with -- modulator compounds --.

Column 10,
Line 56, replace "($CH_2Cl_2$:hexanes, 4:6); $^1$H NMR (400 MHz, $CDCl_3$) δ5" with
-- ($CH_2Cl_2$:hexanes, 4:6); $^1$H NMR (400 MHz,$CDCl_3$) δ --.
Line 57, replace "8.87 (d, J=1.2, 1), 8.43 (dd, J=8.3 and 1.2, 1), 7.58 (d, J=8.6," with
-- 8.87 (d, J=1.2, 1H), 8.43 (dd, J=8.3 and 1.2, 1H), 7.58 (d, J=8.6. --.
Line 58, replace "1), 7.29-7.17 (m, 2), 7.10-7.02 (m, 1) and 3.82 (s, 3H)." with -- 1H), 7.29-7.17 (m, 2H), 7.10-7.02 (m, 1H) and 3.82 (s, 3H). --.

Column 11,
Lines 11 and 12, replace "(d, J=1.1, 1), 8.68 (dd, J=8.5 and 1.1, 1), 8.32 (d, J=8.5, 1), 7.91 (d, J=8.0, 1) and 7.46-7.36 (m, 2)." with -- (d, J=1.1, 1H), 8.68 (dd, J=8.5 and 1.1, 1H), 8.32 (d, J=8.5, 1H), 7.91 (d, J=8.0, 1H) and 7.46-7.36 (m, 2H). --.
Lines 28 and 29, replace "DMSO-$d_6$) δ8.20 (d, J=8.8, 1), 7.97 (d, J=8.0, 1), 7.38 (d, J=8.8, 1), 7.35-7.27 (m, 2), 6.24 (s, 2)." with -- DMSO-$d_6$) δ 8.20 (d, J=8.8, 1H), 7.97 (d, J=8.0, 1H), 7.38 (d, J=8.8, 1H), 7.35-7.27 (m, 2H), 6.24 (s, 2H). --.
Lines 60, 61 and 62, replace, "(400 MHZ, $CDCl_3$) δ8.72 (d, J=8.9, 1), 8.08 (d, J=9.0, 1), 7.79 (bd, J=6.5, 1), 7.54 (s, 1), 7.24-7.18 (m, 2), 5.52 (s, 1), 4.95 (s, 1), 3.81 (s, 3) and 2.14 (s, 3)." with -- (400 MHz, $CDCl_3$) δ 8.72 (d, J=8.9, 1H), 8.08 (d, J=9.0, 1H), 7.79 (bd, J=6.5, 1H), 7.54 (s, 1H), 7.24-7.18 (m, 2H), 5.52 (s, 1H), (s, 1H), 4.95 (s, 1H), 3.81 (s, 3H) and 2.14 (s, 3H) --.

UNITED STATES PATENT AND TRADEMARK OFFICE
CERTIFICATE OF CORRECTION

PATENT NO. : 6,358,947 B1
DATED : March 19, 2002
INVENTOR(S) : L. Zhi et al.

It is certified that error appears in the above-identified patent and that said Letters Patent is hereby corrected as shown below:

Column 12,
Lines 11, 12 and 13, replace "J=8.2, 1), 7.61 (d, J=8.6, 1), 7.46 (d, J=7.5, 1), 7.04-6.93 (m, 2), 6.89 (s, 1), 5.55 (s, 1), 5.10 (d,J=13.5, 1), 5.07 (d, J=13.5, 1), 5.03 (s, 1), 3.79 (s, 3) and 2.01 (s, 3)." with -- J=8.2, 1H), 7.61 (d, J=8.6, 1H), 7.46 (d, J=7.5, 1H), 7.04-6.93 (m, 2H), 6.89 (s, 1H), 5.55 (s, 1H), 5.10 (d, J=13.5, 1H), 5.07 (d, J=13.5, 1H), 5.03 (s, 1H), 3.79 (s, 3H) and 2.01 (s, 3H). --.
Lines 25, 26 and 27, replace "NMR (400 MHz , CDC1$_3$) δ8.71 (bs, 1), 7.58 (d, J=8.4, 1), 7.40 (d, J=7.4, 1), 7.08-6.95 (m, 2) 6.88 (d, J=8.4, 1), 5.24 (s, 2) and 1.84 (s, 6)." with -- NMR (400 MHz, CDC1$_3$) δ 8.71 (bs, 1H), 7.58 (d, J=8.4, 1H), 7.40 (d, J=7.4, 1H), 7.08-6.95 (m, 2H), 6.88 (d, J=8.4, 1H), 5.24 (s, 2H) and 1.84 (s, 6H). --.

Column 13,
Lines 2, 3, 4, and 5, replace "NMR (400 MHz, CDC1$_3$) (rotomers) δ8.13/8.02 (bs, 1), 7.30 (m, 1), 7.17-6.95 (m, 3), 5.61/5.53 (s, 1), 5.21/4.97 (s, 1), 4.50-4.12 (m, 2), 3.79/2.95 (s, 3), 3.62/2.88 (s, 3) and 2.20/2.02 (s, 3)." with -- NMR (400 MHz, CDC1$_3$) (rotomers) δ 8.13/8.02 (bs, 1H), 7.30 (m, 1H), 7.17-6.95 (m, 3H), 5.61/5.53 (s, 1H), 5.21/4.97 (s, 1H), 4.50-4.12 (m, 2H), 3.79/2.95 (s, 3H), 3.62/2.88 (s, 3H) and 2.20/2.02 (s, 3H). --.
Lines 12, 13, 14, and 15, replace "(400 MHz , CDC1$_3$) δ8.15 (d, J=8.7, 1), 7.58 (m, 1), 7.56 (d, J=8.7, 1), 7.15 (dd, J=9.5 and 2.0, 1), 6.89 (s, 1), 5.56 (s, 1), 5.09 (d, J=12, 1), 5.07 (d, J=12, 1), 5.03 (s, 1), 3.79 (s, 3) and 2.00 (s, 3)." with -- (400 MHz, CDC1$_3$) δ 8.15 (d, J=8.7, 1H), 7.58 (m, 1H), 7.56 (d, J=8.7 1H), 7.15 (dd, J=9.5 and 2.0, 1H), 6.89 (s, 1H), 5.56 (s, 1H), 5.09 (d, J=12, 1H), 5.07 (d, J=12, 1H), (s, 1H), 3.79 (s, 3H) and 2.00 (s, 3H). --.
Lines 26, 27 and 28, replace "NMR (400 MHz, CDC1$_3$) δ8.09 (s, 1), 7.53 (d, J=8.3, 1), 7.52 (m, 1), 7.19 (dd, J=9.4 and 1.9, 1), 5.22 (s, 2) and 1.82 (s, 6)." with -- NMR (400 MHz , CDC1$_3$) δ 8.09 (s, 1H), 7.53 (d, J=8.3, 1H), 7.52 (m, 1H), 7.19 (dd, J=9.4 and 1.9, 1H), 5.22 (s, 2H) and 1.82 (s, 6H). --.
Lines 44, 45, and 46, replace "(400 MHz, CDC1$_3$) δ9.97 (d, J=1.8, 1), 9.33 (bs,1), 8.19 (t, J=1.3, 1), 7.90 (d, J=8.4, 1), 7.61 (dd,J=10.3 and 1.3, 1), 7.15 (d, J=8.4, 1), 5.51 (s, 2) and 1.83 (s, 6)." with -- (400 MHz, CDC1$_3$) δ 9.97 (d, J=1.8, 1H), 9.33 (bs, 1H), 8.19 (t, J=1.3, 1H), 7.90 (d, J=8.4, 1H), 7.61 (dd, J=10.3 and 1.3, 1H), 7.15 (d, J=8.4, 1H),  5.51 (s, 2H) and 1.83 (s, 6H).
Line 48, replace "7-Fluoro-9-hydroxyiminomethyl-4,4dimethy5H-chromeno" with -- 7-Fluoro-9-hydroxyiminomethyl-4,4dimethy1-5H-chromeno --.

UNITED STATES PATENT AND TRADEMARK OFFICE
CERTIFICATE OF CORRECTION

PATENT NO. : 6,358,947 B1
DATED : March 19, 2002
INVENTOR(S) : L. Zhi et al.

It is certified that error appears in the above-identified patent and that said Letters Patent is hereby corrected as shown below:

Column 13 cont'd,
Lines 61, 62, and 63, replace "acetone-$d_6$) $\delta$9.27 (s, 1), 8.15 (s, 1), 7.80 (s, 1), 7.78 (d, J=8.3, 1), 9.39 (d, J=11.2, 1), 7.11 (d, J=8.3, 1), 5.39 (s, 2) and 1.81 (s, 6)." with -- acetone-$d_6$) $\delta$ 9.27 (s, 1H), 8.15 (s, 1H), 7.80 (s, 1H), 7.78 (d, J=8.3, 1H), 9.39 (d, J=11.2, 1H), 7.11 (d, J=8.3, 1H), 5.39 (s, 2H) and 1.81 (s, 6H). --.
Line 66, replace "benzo[d]oxazin-2one (Compound 26: Structure 12 of" with -- benzo[d]oxazin-2-one (Compound 26: Structure 12 of --.

Column 14,
Lines 9, 10, and 11, replace "NMR (400 MHz, acetone-$d_6$) $\delta$9.35 (bs, 1), 8.05 (t, J=1.5, 1H), 7.90 (d, J=8.4, 1), 7.59 (dd, J=10.6 and 1.5, 1), 7.15 (d,J=8.4, 1), 5.51 (s,2H) and 1.82 (s, 6)." with -- NMR (400 MHz, acetone-$d_6$) $\delta$ 9.35 (bs, 1H), 8.05 (t, J=1.5, 1H), 7.90 (d, J=8.4, 1H), 7.59 (dd, J=10.6 and 1.5, 1H), 7.15 (d, J=8.4, 1H), 5.51 (s, 2 H) and 1.82 (s, 6H). --.

Column 15,
Line 33, Example 6, replace "hMR," with -- hPR --.
Line 63, Table 1, replace "Ki" with -- $K_i$ --.

Column 16,
Line 44, Table 2, replace "RU486 no 0.1 no 12 no 1500 0.7 1100" with -- RU486 na 0.1 na 12 na 1500 0.7 1100 --.

UNITED STATES PATENT AND TRADEMARK OFFICE
CERTIFICATE OF CORRECTION

PATENT NO. : 6,358,947 B1
DATED : March 19, 2002
INVENTOR(S) : L. Zhi et al.

It is certified that error appears in the above-identified patent and that said Letters Patent is hereby corrected as shown below:

<u>Column 17,</u>
Line 25, Example 7, replace "Silicone dioxide, filmed" with -- Silicone dioxide, fumed --.

Signed and Sealed this

Twenty-fourth Day of September, 2002

*Attest:*

*Attesting Officer*

JAMES E. ROGAN
*Director of the United States Patent and Trademark Office*